(12) United States Patent
Posmantur et al.

(10) Patent No.: US 6,545,019 B2
(45) Date of Patent: Apr. 8, 2003

(54) METHOD OF MODULATING MICROGLIAL ACTIVATION FOR THE TREATMENT OF ACUTE AND CHRONIC NEURODEGENERATIVE DISORDERS

(75) Inventors: Rand M. Posmantur, Branford, CT (US); Lav Kumar Parvathenani, Rocky Hill, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/899,657

(22) Filed: Jul. 5, 2001

(65) Prior Publication Data

US 2002/0022650 A1 Feb. 21, 2002

Related U.S. Application Data

(60) Provisional application No. 60/218,085, filed on Jul. 13, 2000, and provisional application No. 60/261,332, filed on Jan. 12, 2001.

(51) Int. Cl.$^7$ ............................................... A61K 31/47
(52) U.S. Cl. ...................................................... 514/311
(58) Field of Search ......................................... 514/311

(56) References Cited

U.S. PATENT DOCUMENTS 6,136,839 A * 10/2000 Isakson et al. .............. 514/406

OTHER PUBLICATIONS

Database Medline on STN, (Columbus, OH, USA), No. 1999065, Ramoner, R. et al. 'Nordihydroguaiaretic acid blocks secretory and endocytic pathways in human dendritic cells,' abstract, J. Leukocyte Biology, Dec. 1998, 64(6), 747–52.

Database Medline on STN, (Columbus, OH, USA), No. 98181109, Abraham, W. et al. 'The effects of ML 3000 on antigen–induced responses in sheep,' abstract, Pulmonary Pharmacology Ther., Jun. 1997, 10(3), 167–73.

Database CAPLUS on STN, (Columbus, OH, USA), Lee, S. et al. 'Inhibition of 5–lipoxygenase blocks IL–1.beta.–induced vascular adhesion molecule–1 gene expression in human endothelial cells,' abstract, J. Immunol., 1997, 158(7), 3401–3407.

Database Medline on STN, (Columbus, OH, USA), No. 20178139, Jobin, C. et al. 'The I kappa B/NF–kappa B system: a key determinant of mucosalinflammation and protection,' abstract, Am. J. Physiology. Cell Physiology, Mar. 2000, 278(3), C451–62.

Simon, Lee, "Role and regulation of cyclooxygenase–2 during inflammation," American Journal of Medicine, 106, 37S–42S, 1999.

Versteeg, Henri H., et al., Cyclooxygenase–dependent signaling: molecular events and consequences, FEBS Letters, 445, 1999, pp. 1–5.

Lipoxygenases and Their Metabolites, Plenum Press, NY. Eds. Nigam and Pace–Asciak, 1999, pp. 5–28.

Tomimoto, Hidekazu, et al., "Cyclooxygenase–2 is also induced in microglia during chronic cerebral ischemia in humans," Acta Neuropathol (Berl), 1, pp. 26–30, 2000.

* cited by examiner

Primary Examiner—Theodore J. Criares
Assistant Examiner—Jennifer Kim
(74) Attorney, Agent, or Firm—Shah R. Makujina

(57) ABSTRACT

The present invention provides methods of modulating or inhibiting microglia activation comprising the administration of a compound capable of inhibiting 5-LOX, FLAP, attenuating degradation of IκBα or inhibiting nuclear translocation of the NF-κB active complex for the treatment of Alzheimer's disease, brain ischemia, traumatic brain injury, Parkinson's Disease, Multiple Sclerosis, ALS, subarachnoid hemorrhage or other disorders associated with excessive production of inflammatory mediators in the brain.

5 Claims, 14 Drawing Sheets

Figure 1A:
Figure 1B:
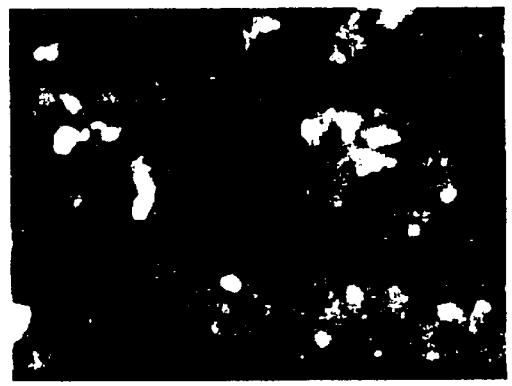
Figure 1C:
Figure 1D:
Figure 1E:
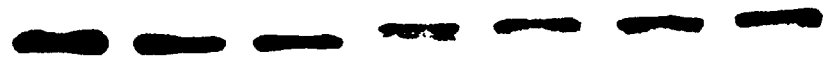
Figure 2A:
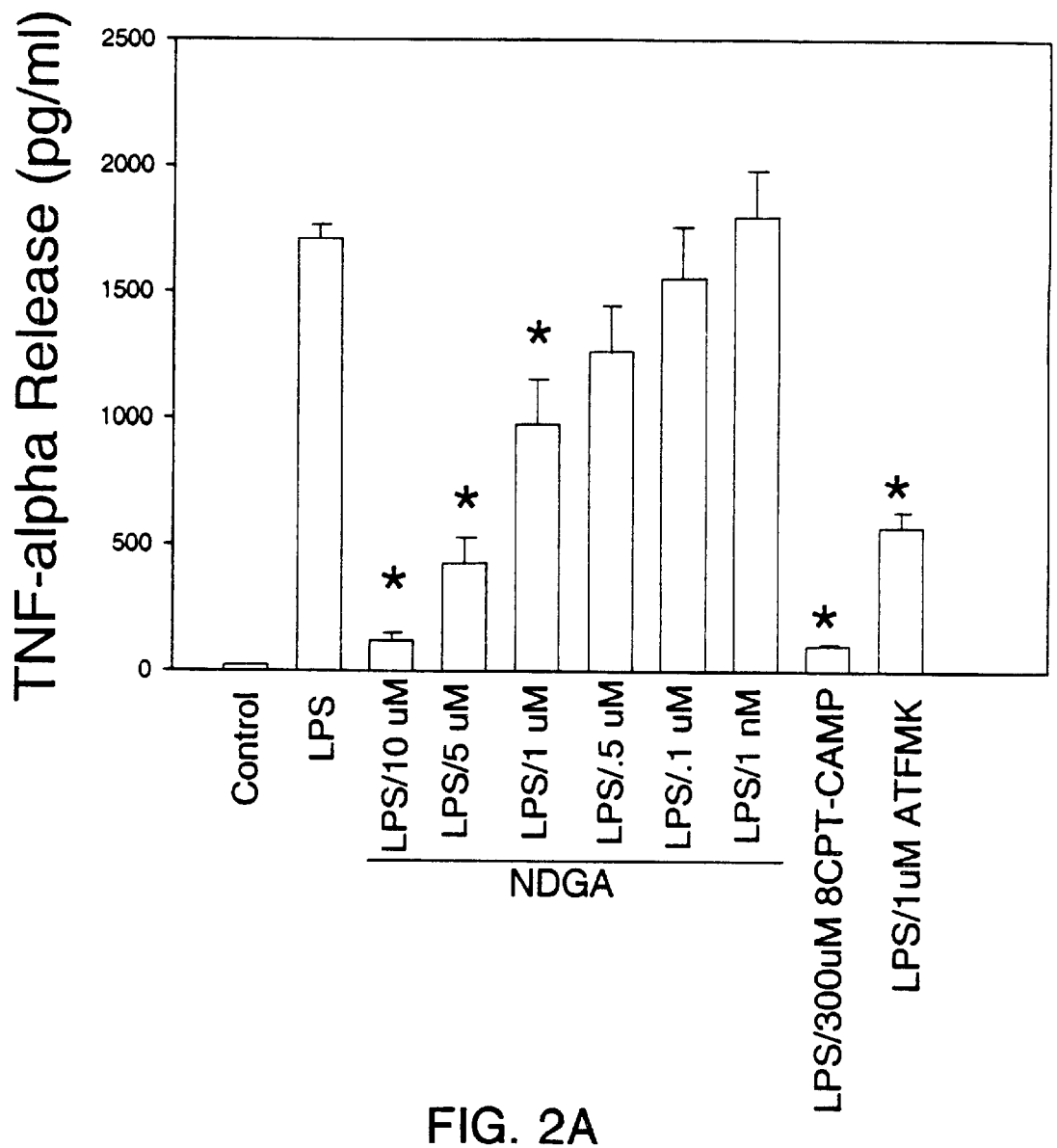
Figure 2B:
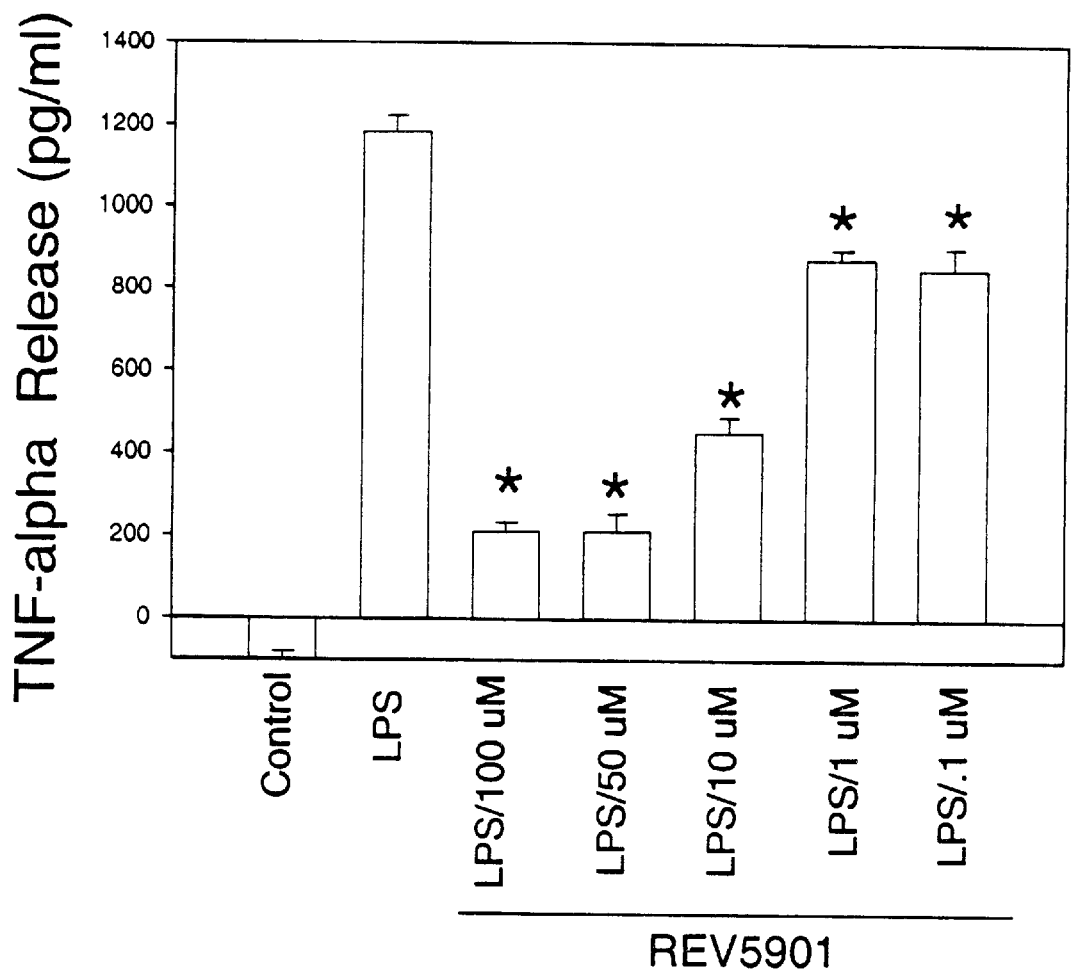
Figure 2C:
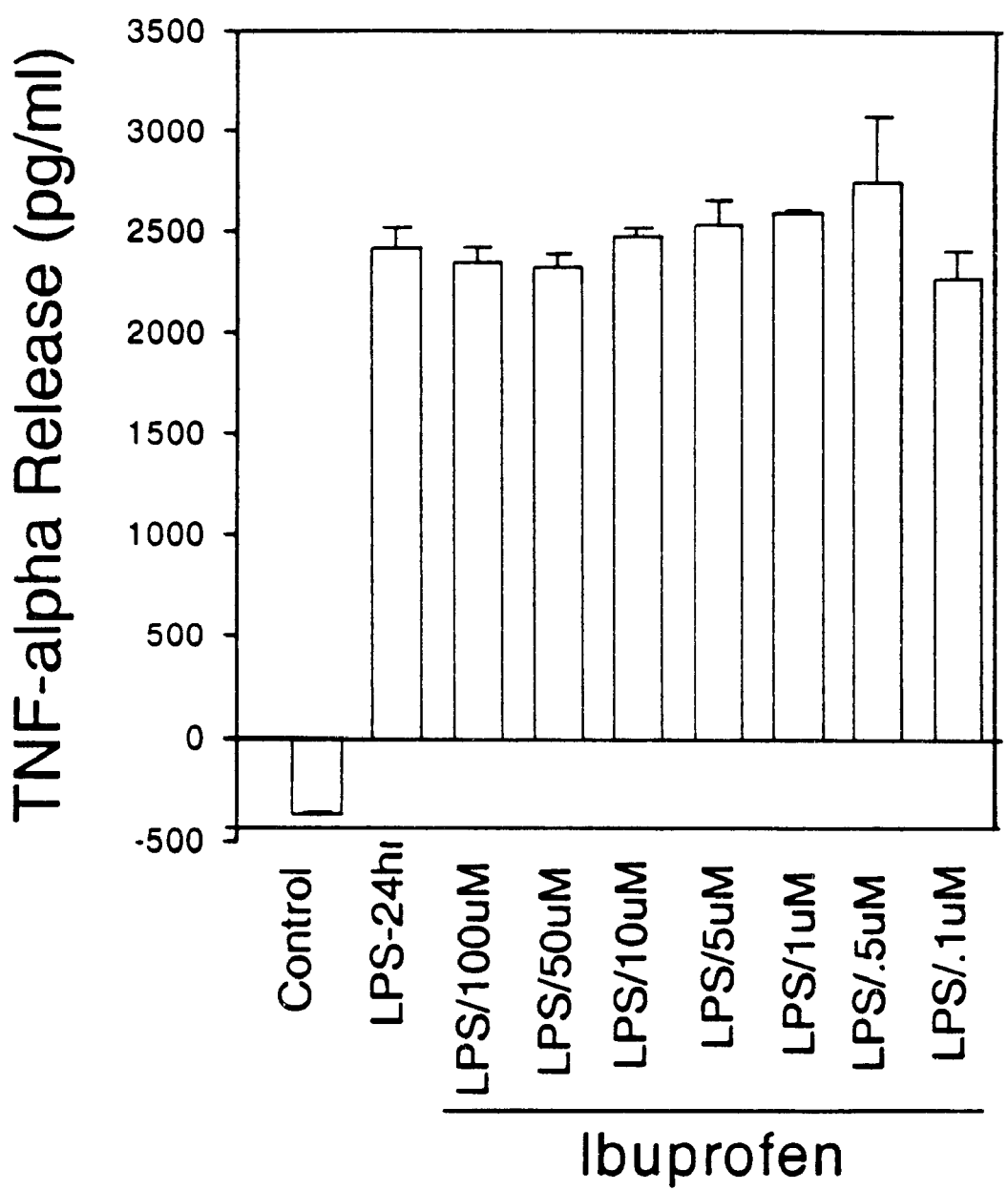
Figure 2D:
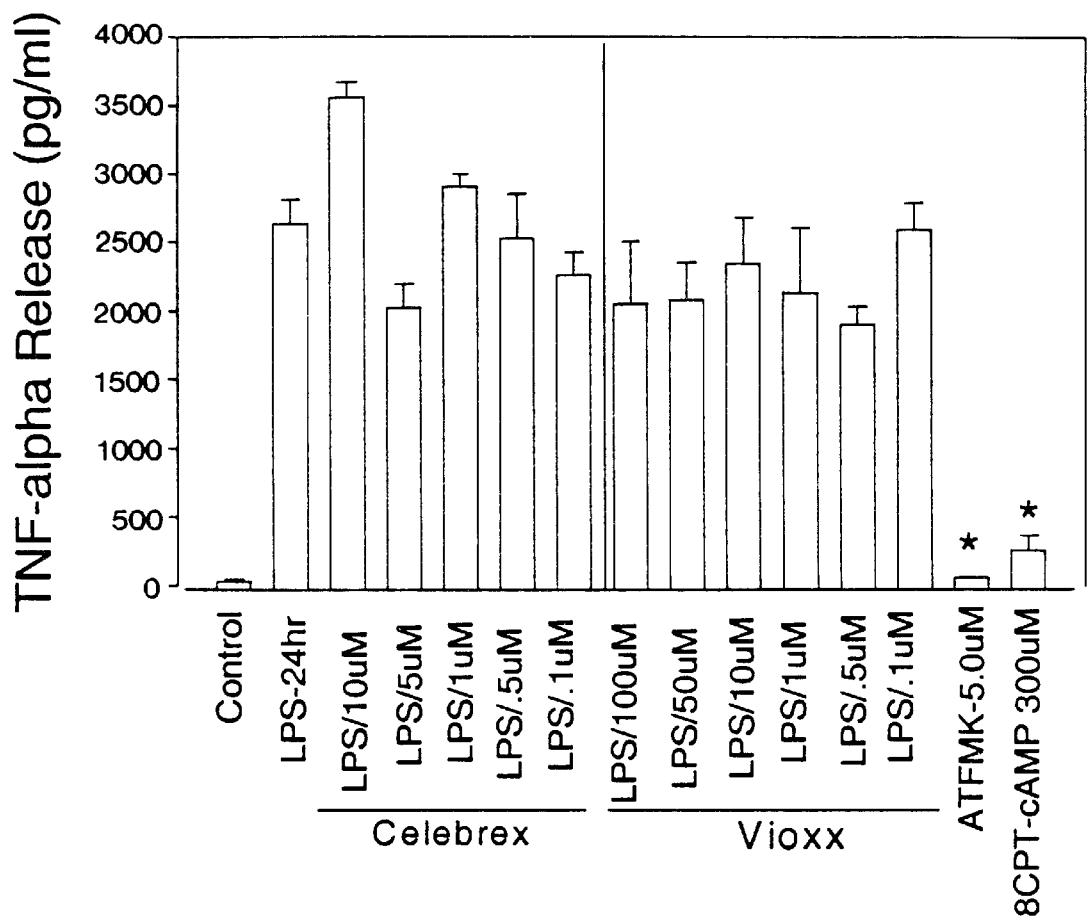

| TIME (MIN) | 5 | 5 | 10 | 20 | 30 | 45 | 60 |
|---|---|---|---|---|---|---|---|
| LPS | − | + | + | + | + | + | + |

METHOD OF MODULATING MICROGLIAL ACTIVATION FOR THE TREATMENT OF ACUTE AND CHRONIC NEURODEGENERATIVE DISORDERS

CROSS REFERENCE TO RELATED APPLICATIONS

This non-provisional application claims priority from provisional applications U.S. Ser. No. 60/218,085 filed Jul. 13, 2000 and U.S. Ser. No. 60/261,332 filed Jan. 12, 2001.

FIELD OF THE INVENTION

The present invention comprises methods of treating various acute and chronic central nervous system disorders by the administration of FLAP or 5-lipoxygenase inhibitors.

BACKGROUND OF THE INVENTION

Acute and chronic brain injuries can activate resident microglia (resident macrophage-like cells found in the central nervous system) as well as recruit peripheral immune cells to injured brain regions that can exacerbate neuronal damage. Inflammatory processes can induce cell death by (a) the release of proteases and free radicals that induce lipid peroxidation, (b) direct cytotoxic effects or (c) by the phagocytosis of sublethally injured neurons. The attenuation of microglia and peripheral immune cell activation has been correlated with significant neuronal protection in pre-clinical studies of ischemia, traumatic brain injury, spinal cord injury and Alzheimer's disease.

Oxygenase enzymes like cycloxygenase and lipoxygenase can initiate the conversion of arachidonic acid to physiological important metabolites. Cycloxygenase (COX; prostaglandin H2 synthase) is responsible for the formation of prostaglandins and thomboxanes. See Versteeg, H. Van, van Bergen en Henegouwen, M. P. V., van Deventer, S. J. W. and Peppelenbosch, M. P. (1999). Cyclooxygenase-dependent signaling: :molecular events and consequences. *FEBS letters* 445: 1–5. Lipoxygenase is responsible for the conversion of arachidonic acid to leukotrienes. Lipoxygenases and Their Metabolites, Plenum Press, N.Y. Eds. Nigam and Pace-Asciak. (1999). It is hypothesized that prostaglandins are an important step in transducing immune stimuli into CNS responses. There are two known isozymes of COX currently known COX-1 (constituitively expressed) and COX-2 (induction in response to immune stimuli). It has been established that COX-1 and COX-2 are found to be induced and constituitively expressed in peripheral immune cells as well as brain, with neuronal expression of COX-2 being enhanced following various CNS insults including cerebral ischemia. Tomimoto, H., Akiguchi, I. Watkita, H., Lin, J. X., Budka, H. Cyclooxygenase-2 is also induced in microglia during chronic cerebral ischemia in humans. *Acta Neuropathol* (Berl) 1: 26–30 (2000).

However, little is known about the role of lipoxygenases (or subsequent metabolites including hydroxyeicosatetraenoic acids (HETEs), leukotrienes, lipoxines, and hepoxilins) in regulating brain inflammation or neurodegeneration. There are currently four known human lipoxygenases (5, 8, 12, and 15-lipoxygenase). All isoforms share a common substrate as well as oxygenase activity but differ greatly in sequence. Although, the role of prostaglandins and COX-2 in modulating inflammation and pain has been well elucidated, the importance of LOX enzymes (specifically 5-LOX or 5-lipoxygenase) in brain following injury is still unresolved. Simon, L. S. Role and regulation of cyclooxygenase-2 during inflammation *American Journal of Medicine* 106: 37S–42S (1999).

SUMMARY OF THE INVENTION

Thus, according to a first embodiment of a first aspect of the present invention is provided a method of modulating or inhibiting microglia activation comprising the administration to a human in need thereof a compound capable of inhibiting 5-LOX.

According to another embodiment of the first aspect of the present invention is provided a method of modulating or inhibiting microglia activation comprising the administration to a human in need thereof a compound capable of selectively inhibiting 5-LOX over COX-2.

According to another embodiment of the first aspect of the present invention is provided a method of modulating or inhibiting microglia activation comprising the administration to a human in need thereof a compound capable of inhibiting FLAP.

According to another embodiment of the first aspect of the present invention is provided a method of modulating or inhibiting microglia activation comprising the administration to a human in need thereof para-REV5901 (L-655,238), Bay-x-1005, ML-3000, NDGA or ZILEUTON®.

According to a first embodiment of a second aspect of the present invention is provided a method of inhibiting the release of pro-inflammatory substances from activated microglial cells comprising the administration to a human in need thereof a compound capable of inhibiting 5-LOX.

According to another embodiment of a second aspect of the present invention is provided a method of inhibiting the release of pro-inflammatory substances from activated microglial cells comprising the administration to a human in need thereof a compound capable of selectively inhibiting 5-LOX over COX-2.

According to another embodiment of a second aspect of the present invention is provided a method of inhibiting the release of pro-inflammatory substances from activated microglial cells comprising the administration to a human in need thereof a compound capable of inhibiting FLAP.

According to another embodiment of a second aspect of the present invention is provided a method of inhibiting the release of pro-inflammatory substances from activated microglial cells comprising the administration to a human in need thereof para-REV5901 (L-655,238), Bay-x-1005, ML-3000, NDGA or ZILEUTON®.

According to a first embodiment of a third aspect of the present invention is provided a method of treating Alzheimer's disease, brain ischemia, traumatic brain injury, Parkinson's Disease, Multiple Sclerosis, ALS, subarachnoid hemorrhage or other disorders associated with excessive production of inflammatory mediators in the brain comprising the administration to a human in need thereof a compound capable of inhibiting 5-LOX.

According to another embodiment of a third aspect of the present invention is provided a method of treating Alzheimer's disease, brain ischemia, traumatic brain injury, Parkinson's Disease, Multiple Sclerosis, ALS, subarachnoid hemorrhage or other disorders associated with excessive production of inflammatory mediators in the brain comprising the administration to a human in need thereof a compound capable of 5-LOX over COX-2.

According to another embodiment of a third aspect of the present invention is provided a method of treating Alzheimer's disease, brain ischemia, traumatic brain injury, Parkinson's Disease, Multiple Sclerosis, ALS, subarachnoid hemorrhage or other disorders associated with excessive production of inflammatory mediators in the brain comprising the administration to a human in need thereof a compound capable of inhibiting FLAP.

According to another embodiment of a third aspect of the present invention is provided a method of treating Alzheimer's disease, brain ischemia, traumatic brain injury, Parkinson's Disease, Multiple Sclerosis, ALS, subarachnoid hemorrhage or other disorders associated with excessive production of inflammatory mediators in the brain comprising the administration to a human in need thereof para-REV5901 (L-655,238), Bay-x-1005, ML-3000, NDGA or ZILEUTON®.

According to a first embodiment of a fourth aspect of the present invention is provided a method of attenuating degradation of IκBα comprising the administration to a human in need thereof a compound capable of inhibiting 5-LOX.

According to another embodiment of a fourth aspect of the present invention is provided a method of attenuating degradation of IκBα comprising the administration to a human in need thereof a compound capable of selectively inhibiting 5-LOX over COX-2.

According to another embodiment of a fourth aspect of the present invention is provided a method of attenuating degradation of IκBα comprising the administration to a human in need thereof a compound capable of inhibiting FLAP.

According to another embodiment of a fourth aspect of the present invention is provided a method of attenuating degradation of IκBα comprising the administration to a human in need thereof para-REV5901 (L-655,238), Bay-x-1005, ML-3000, NDGA or ZILEUTON®.

According to a first embodiment of a fifth aspect of the present invention is provided a method of inhibiting nuclear translocation of the NF-κB active complex comprising the administration to a human in need thereof a compound capable of inhibiting 5-LOX.

According to another embodiment of a fifth aspect of the present invention is provided a method of inhibiting nuclear translocation of the NF-κB active complex comprising the administration to a human in need thereof a compound capable of selectively inhibiting 5-LOX over COX-2.

According to another embodiment of a fifth aspect of the present invention is provided a method of inhibiting nuclear translocation of the NF-κB active complex comprising the administration to a human in need thereof a compound capable of inhibiting FLAP.

According to another embodiment of a fifth aspect of the present invention is provided a method of inhibiting nuclear translocation of the NF-κB active complex comprising the administration to a human in need thereof para-REV5901 (L-655,238), Bay-x-1005, ML-3000, NDGA or ZILEUTON®.

Other embodiments of the invention comprise two or more embodiments or elements thereof suitably combined.

Yet other embodiments and aspects of the invention will be apparent according to the description provided below.

DETAILED DESCRIPTION OF THE INVENTION

As used herein "a compound capable of selectively inhibiting 5-LOX over COX-2" means a compound having 1 to 500-fold or more, particularly 1 to 50-fold and more particularly 1 to 10-fold selectivity for 5-LOX over COX-2 as measured by the ability to attenuate the production of arachidonic acid metabolites from cellular suspensions (derived from blood or cell lines) stimulated with ionophore A23187 as previously described (Salari et al., 1984, Prostaglandins and Leukotrienes, Vol 13: 53–60; Menard et al., 1990, Br. J. Pharmacol 100: 15–20) incorporated by reference herein. For instance, 5-HETE and LTB4 are arachidonic acid metabolites derived from 5-LOX and 12-hydroxy-heptadecatrienoic (HHT) is an arachidonic acid metabolite for cycloxygenase activity. Alternatively, COX-2 can be specifically assessed by the ability to attenuate the production of the arachidonic acid metabolite, PGE2, from cellular suspensions (derived from blood or cell lines) stimulated with the LPS (Laufer et al., 1999, Inflammation Research, 48: 133–138; Horton et al., 1999; Anal Biochem 271:18–28).

As used herein "FLAP" means 5-LOX activating protein. Compounds that inhibit FLAP can be measured by the ability to inhibit photoaffinity labeling of a source of purified FLAP (i.e. rat or human). In addition, FLAP inhibitors are confirmed if there is a correlation in the inhibition of leukotriene synthesis in vitro cell based assays (i.e. Human PMN leukotriene synthesis) (Evans et al., 1991, Molecular Pharmacology 40:22–27).

As used herein "inflammatory mediators in the brain" includes but is not limited to cytokines, chemokines, prostaglandins and leukotrienes.

As used herein "pro-inflammatory substances" includes but is not limited to TNF-alpha, nitrite, NO, IL-6, IL-1, 5-HETE, LTB4, LTA4 and other inflammatory substances.

Bay-x-1005 ($C_{23}H_{23}NO_3$) is a selective inhibitor of FLAP. See *Drugs Fut* 1995, 20:996 and *Drugs Fut* 2000 25(10):1084.

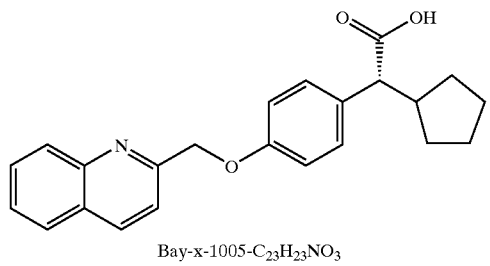

Bay-x-1005-$C_{23}H_{23}NO_3$

ML-3000 is an inhibitor of both COX and LOX. See *Drugs Fut* 1995 20:1007 and *Drugs Fut* 25(10):1093.

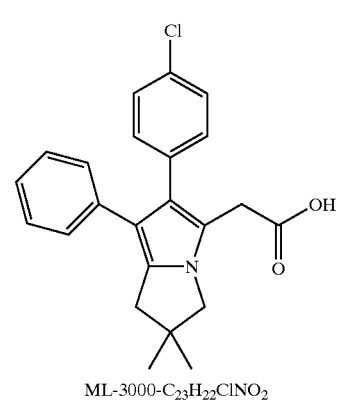

ML-3000-$C_{23}H_{22}ClNO_2$

REV5901-para-isomer (L-655,238- IC50=0.1 uM—5-LOX) is a selective 5-lipoxygenase activating protein inhibitor (FLAP) with a quinoline structure. It has been reported that FLAP inhibitors with this basic chemical structure interfere with 5-LOX and FLAP protein interactions preventing a required cellular translocation of 5-LOX. Moreover, it has been shown that compounds with the quinoline chemical structure do not affect other routes of arachidonic acid metabolism including known cycloxygenase and other lipoxygenases proteins (Evans et al., 1991, Molecular Pharmacology 40:22–27; Hutchinson, A. W. 1991, Trend in Pharmacological Studies, 12: 68–70).

NDGA is a selective 5-lipoxygenese over cycloxgenase inhibitor (IC50=0.2 uM—5-LOX, IC50=100 uM—COX)-Salari et al, 1984.

We have discovered that indirectly or directly inhibiting 5-lipoxygenase can preferentially attenuate pro-inflammatory cytokine release from activated rat microglia cells in comparison to COX-2 inhibition. While not intending to limit the scope of the invention to any particular mechanism the following description is provided. Cytosolic Ca2+ dependent type IV phospholipase A2 (CPLA2) generates intracellular arachidonic acid (AA). AA is converted to pro-inflammatory prostaglandins, thromboxanes, and leukotrienes by either cycloxygenases (COX) or lipoxygenases (LOX).

Since cytosolic phospholipase A2 (cPLA$_2$) is one of the major enzymes involved in the generation of AA, the effect of lipopolysaccharide (LPS) on cPLA$_2$ was determined. Indirect immunofluorescence with a cPLA$_2$ specific monoclonal antibody revealed that cPLA$_2$ was localized primarily in the cytosol in untreated cells. Upon stimulation with LPS, cPLA$_2$ redistributed to form punctate bodies within 15 minutes and returned to a control immuno-staining pattern by 60 minutes (the transient redistribution of cPLA2 to punctate bodies is an intracellular event associated with higher activity). The activity of cPLA$_2$ can also be enhanced by phosphorylation (Lin et al., 1993). Phosphorylated cPLA$_2$ can be distinguished from unphosphorylated cPLA$_2$ by migration on SDS-PAGE. Immunoblotting revealed that cPLA$_2$ in control cells was predominately unphosphorylated. Following LPS challenge cPLA$_2$ shifted to a phosphorylated form between 10–20 minutes post-challenge. Importantly, CPLA2 inhibitors, i.e., ATFMK (arachidonyltrifluoromethyl ketone) and BMS 229724 have shown significant dose-dependent inhibition of TNF-alpha and nitrite release in LPS activated microglia. The redistribution and phosphorylation of cPLA$_2$ as well as, the attenuation of TNF-alpha and nitrite by cPLA2 inhibitors provide several lines of evidence for the activation of cPLA$_2$ in LPS treated microglia.

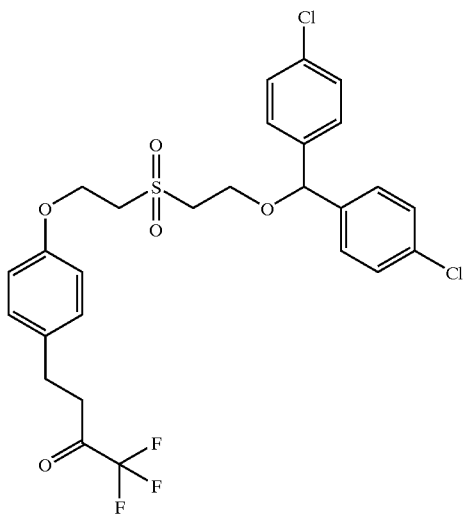

BMS-229724 (WO 99/15129)

COX-2 inhibitors rofecoxib (VIOXX®) and celecoxib (CELEBREX®) had no significant effect on pro-inflammatory release on activated microglia. Importantly, para-REV5901 (α-pentyl-4-(3-quinolinylmethyl) benzenemethanol) a 5-LOX activating protein inhibitor and NDGA (nordihdroguaiaretic acid) a 5-LOX inhibitor, dose dependently inhibited TNF-alpha release and nitrite to near control levels following LPS challenge in microglia cells.

To further validate the role of 5-LOX in pro-inflammatory cytokine release transcriptional regulators of TNF-alpha and NO were examined. Lipoxygenases can activate NFκB mediated transcription via the generation of reactive oxygen intermediates (Lee et al., 1997; Bonizzi et al., 1999). Both the TNFα gene and inducible nitric oxide synthase (iNOS) gene contain NF-κB binding elements in their promoter sequences and activation of NF-κB is crucial for gene transcription (Goldfeld et al., 1990; Drouet et al., 1991; Xie et al., 1994). Hence the effects of inhibiting NF-κB mediated transcription using two distinct inhibitors was assessed with BAY 11–7085 an irreversible inhibitor of IκBα phosphorylation ([IC$_{50}$-10μM] a biochemical event associated NF-κB activity) and NF-κB SN-50 a cell permeable peptide which inhibits translocation of NF-κB active complex into the nucleus (a required intracellular event associated with NF-κB activity; Lin et al., 1995; Pierce et al., 1997). Both BAY 11–7085 and NF-κB SN-50 inhibited LPS induced TNFα and NO release to control levels.

To further characterize the involvement of NF-κB in microglial signaling, the effect of LPS on the degradation of IκBα and NF-κB (p65) translocation from the cytosol to the nucleus was also determined. It was observed that IκBα was rapidly degraded within 20 minutes following LPS activation and reappeared to control levels by 60 minutes. Consistent with these observations, indirect immunofluorecence with a p65 antibody indicated that in control cells p65 was primarily localized in the cytosol, but after stimulation with LPS p65 rapidly translocated to the nucleus. These results demonstrate that NF-κB mediated transcription can play a role in microglia activation.

To determine whether cPLA$_2$ and 5-LOX regulate TNFα and NO release by influencing NF-κB activation, the effects of cPLA$_2$ and 5-LOX inhibitors on IκBα degradation and nuclear translocation of NF-κB were examined. ATFMK and para-REV5901 attenuated the degradation of IκBα following LPS stimulation. ATFMK and para-REV5901 also delayed the translocation of NF-κB into the nucleus. These results demonstrate that both cPLA$_2$ and 5-LOX inhibitors attenuate the release of TNFα and NO by delaying IκBα degradation and interfering with NF-κB activation.

These data collectively represent that 5-LOX (via CPLA2, AA, and NF-κB signaling) is a preferential target over COX-2 in modulating or inhibiting microglia activation. Consequently, modulating either 5-LOX alone or in conjunction with COX-2 could have direct effects in enhancing neuronal survival in acute and chronic CNS diseases including Alzheimer's disease, brain ischemia, traumatic brain injury, Parkinson's Disease, Multiple Sclerosis, ALS, and subarachnoid hemorrhage.

Lin L L, Wartmann M, Lin A Y, Knopf J L, Seth A, Davis R J (1993) cPLA2 is phosphorylated and activated by MAP kinase. Cell 72:269–278.

Lee S, Felts K A, Parry G C, Armacost L M, Cobb R R (1997) Inhibition of 5-lipoxygenase blocks IL-1 beta-induced vascular adhesion molecule-1 gene expression in human endothelial cells. J Immunol 158:3401–3407.

Bonizzi G, Piette J, Schoonbroodt S, Greimers R, Havard L, Merville M P, Bours V (1999) Reactive oxygen intermediate-dependent NF-kappaB activation by interleukin-1 beta requires 5-lipoxygenase or NADPH oxidase activity. Mol Cell Biol 19:1950–1960.

Goldfeld A E, Doyle C, Maniatis T (1990) Human tumor necrosis factor alpha gene regulation by virus and lipopolysaccharide. Proc Natl Acad Sci U S A 87:9769–9773.

Drouet C, Shakhov A N, Jongeneel C V (1991) Enhancers and transcription factors controlling the inducibility of the tumor necrosis factor-alpha promoter in primary macrophages. J Immunol 147:1694–1700.

Xie Q W, Kashiwabara Y, Nathan C (1994) Role of transcription factor NF-kappa B/Rel in induction of nitric oxide synthase. J Biol Chem 269:4705–4708.

Lin Y Z, Yao S Y, Veach R A, Torgerson T R, Hawiger J (1995) Inhibition of nuclear translocation of transcription factor NF-kappa B by a synthetic peptide containing a cell membrane-permeable motif and nuclear localization sequence. J Biol Chem 270:14255–14258.

Pierce J W, Schoenleber R, Jesmok G, Best J, Moore S A, Collins T, Gerritsen M E (1997) Novel inhibitors of cytokine-induced IkappaBalpha phosphorylation and endothelial cell adhesion molecule expression show anti-inflammatory effects in vivo. J Biol Chem 272:21096–21103.

Isolation of Microglia from Rat Brains:

Rat microglia were prepared from two day old rat pups. Pup brains were removed and the meninges were gently removed. Once sufficient amount of brains were collected, brains were minced with a blunt scissors (10 times) and transferred to a 15ml conical tube with a pasteur pipette and titurated 25 times. Dissociated cells were then centrifuged at 1000 RPM for 10 minutes (RT). The supernatant was removed and 2 mls of fresh media was added. The resultant cell suspension was titurated 10 times. Following titration the cell suspension was plated in a T175 cm$^2$ culture flasks at a density of 4 brains per flask in 25 mls. MEM media was used for the experiments, supplemented with 10% FBS, 100 i.u.penicillin, 100 i.u.streptomycin and L-Glutamine. Microglia were isolated on day 14 by shaking on an orbital rotation shaker. The purity of the cultures was 98–100% as determined by immunostaining with ED-40 antibody.

Rat Microglia Cell Activation and Drug Exposure

Endotoxin (LPS) at a concentration of a 100 ng/ml were used for activation of rat microglia cells. This concentration had previously shown to be effective in inducing TNF-alpha and Nitrite release. All assays were performed in 48 well plates (Becton Dickinson) at ~2×10$^5$ cells or 0.5×10$^5$ per 1 ml per well in 10% MEM media. Microglia cells were pre-incubated 1 hr prior to LPS challenge with either vehicle (0.1%DMSO) or test compound in DMEM containing 10%FBS (microglia) or RPMI containing 10%FBS (THP-1 monocytes). Supernatants from LPS activated rat microglia were collected at 24 hrs post-LPS challenge.

TNF-alpha ELISA

Collected supernatants were assayed for TNF-alpha using a Pharmingen OPtEIA Rat (microglia).

Nitrite Assay

Nitrite assay was performed in a 96 well plate using a Modified Griess Reagent (Sigma). In brief, a 100 ul of Modified Griess Reagent was added to a 100 ul of collected supernatant. Samples were read at a wavelength of 540nM. All values were calculated against a NaNO2 standard curve.

Immunofluorescence

Cells were washed once with PBS, fixed and permeabilized with ice cold methanol (100%) for 5 minutes and washed 3× in PBS for 10 min. The cover slips were blocked for 1 hour in 10% serum/PBS (serum derived from animal in which secondary antibody was generated), incubated for 2–3 hours in primary antibody solution (1:50 dilution in 1.5% serum/PBS) and washed 3× in PBS for 10 min. Secondary antibody linked to fluorescein was applied for one hour (1:100 dilution in 1.5% serum/PBS) and washed 3× in PBS for 10 min. If the nucleus was stained, the cells were incubated for 15 minutes with DAPI (1:10000) at 37° C. and washed. The coverslips were then mounted onto glass slides using mounting media and viewed under a fluorescence microscope.

Immunoblotting

Immunoblotting was carried out as described previously (Parvathenani et al., 2000). Briefly 25μg of protein was fractionated on a 4–20% tris-glycine gel (NOVEX, Calif.) and transferred to PVDF membrane (NOVEX, Calif.). The membrane was probed with a polyclonal antibody specific for IκBα. To distinguish between the phosphorylated and non-phosphorylated forms of cPLA$_2$, 50μg of protein was run on an 8% tris-glycine gel (Novex, Calif.) for 4.5 hours at 125V, transferred and probed with a monoclonal antibody specific for cPLA$_2$.

Materials

NDGA (nordihdroguaiaretic acid), para-REV5901 (α-pentyl-4-(3-quinolinylmethyl)benzenemethanol), ATFMK (arachidonyltrifluoromethyl ketone) was obtained from Calbiochem (San Diego, Calif.). Ibuprofen and LPS was purchased from Sigma (St. Louis, Mo.). BMS 229724 was synthesized at Bristol-Myers Squibb. NF-κB SN50 and (E)3-((4-t-Butylphenyl)sulfonyl)-2-propenenitrile (BAY-11–7085) were obtained from Biomol (Plymouth Meeting, Pa.).

FIGURES

The data represents mean±S.D. of triplicate samples of an experiment repeated at least three times. *=Statistically significant ($p<0.05$) in comparison to LPS (positive control).

FIGS. 1A–E Legend

Microglia were treated with 100 ng/ml of LPS for various periods of time following which A–D. cPLA$_2$ distribution was assessed by indirect immunofluorescence (1A) control, (1B) LPS-15 min, (1C) LPS-15 min, (1D) LPS-60 min, (1E) whole cell lysates were prepared and run on SDS-PAGE, transferred and probed with a cPLA$_2$ antibody.

FIGS. 2A–D Legend 5-lipoxygnease inhibitor (NDGA, 2A) and 5-lipoxygenase activating protein inhibitor (para-REV5901, 2B) significantly inhibited TNF-alpha release, however, COX-2 inhibitors Ibuprofen (2C), Vioxx (2D), and Celebrex (2D) failed to produce any reduction in TNF-alpha release in rat primary microglia cells following LPS activation.

Figure 3A:
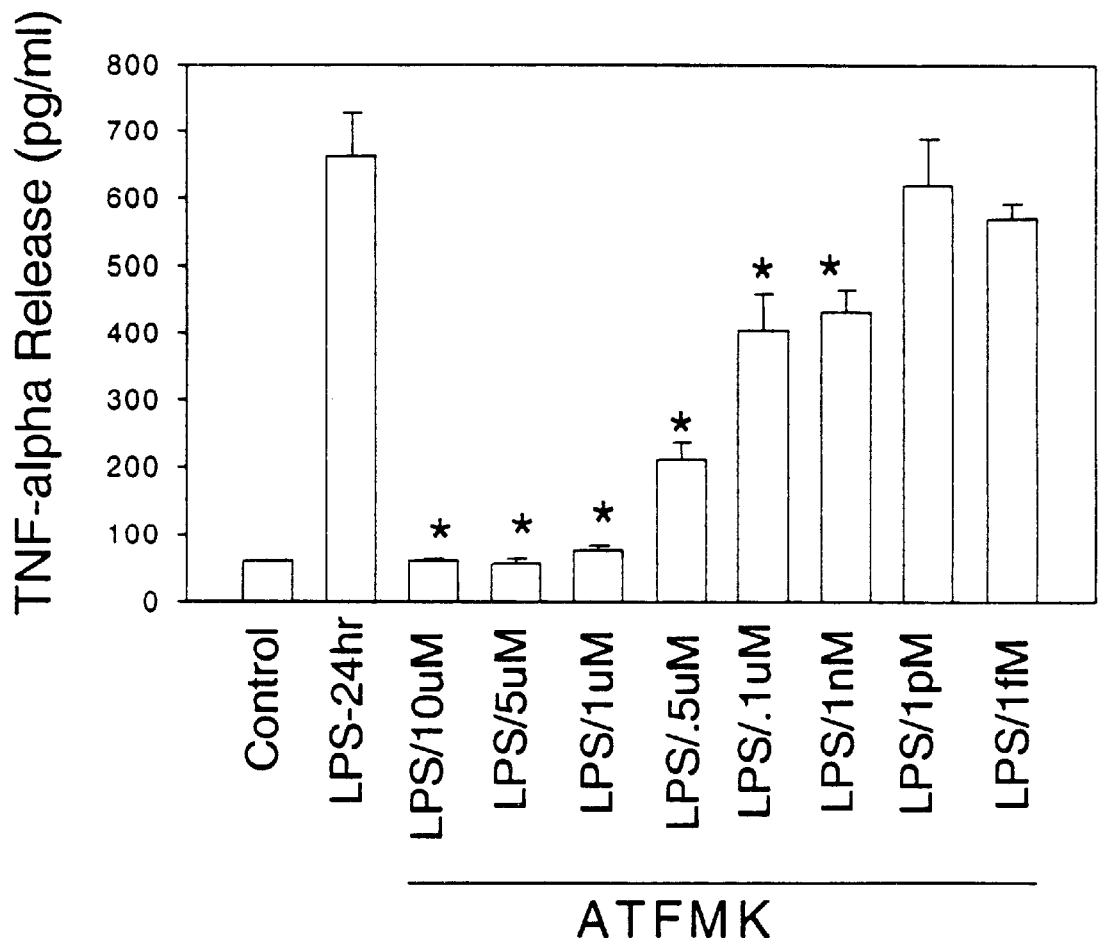
Figure 3B:
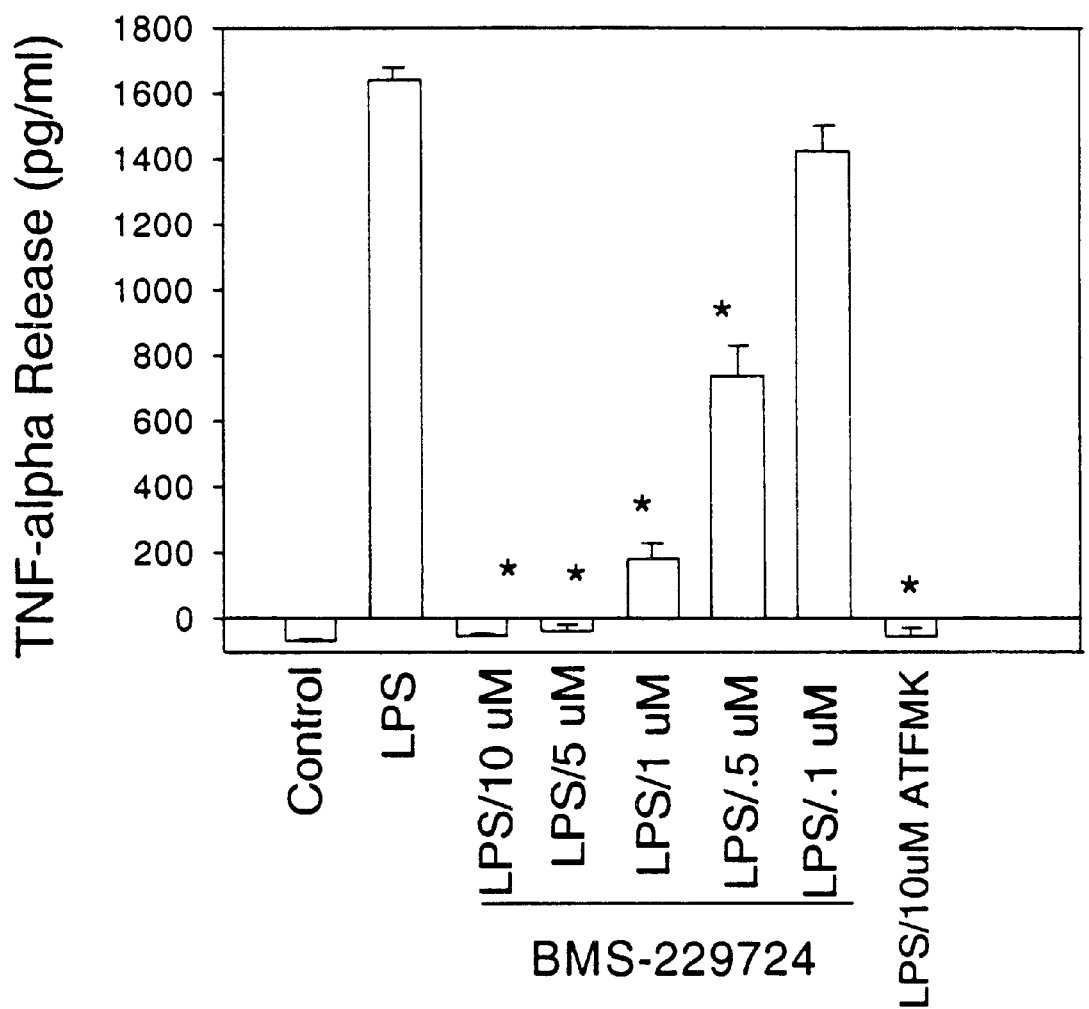

FIGS. 3A–B Legend cPLA2 inhibitors ATFMK (3A) and BMS-229724 (3B) significantly inhibited TNF-alpha release in rat primary microglia cells following LPS activation.

Figure 4A:
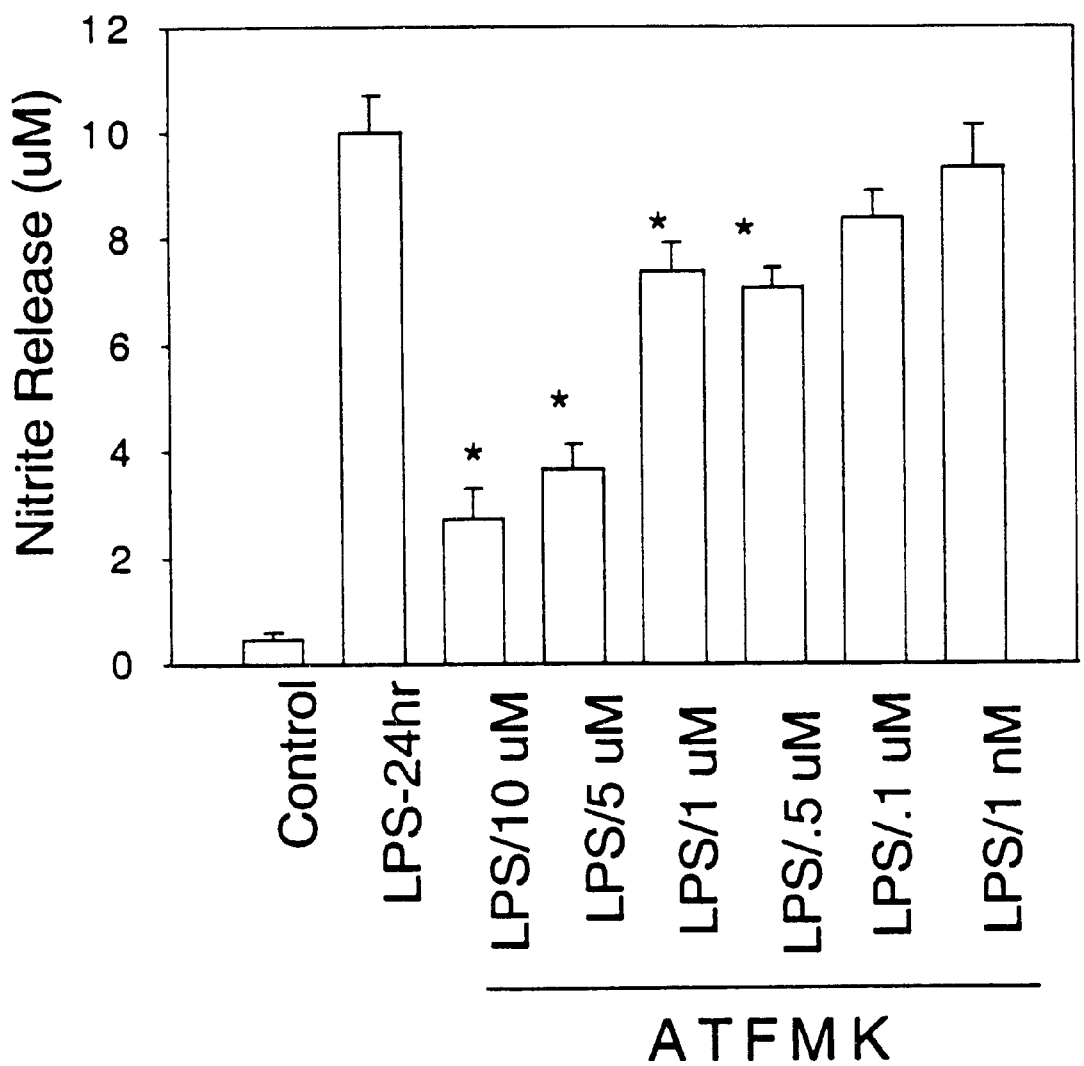
Figure 4B:
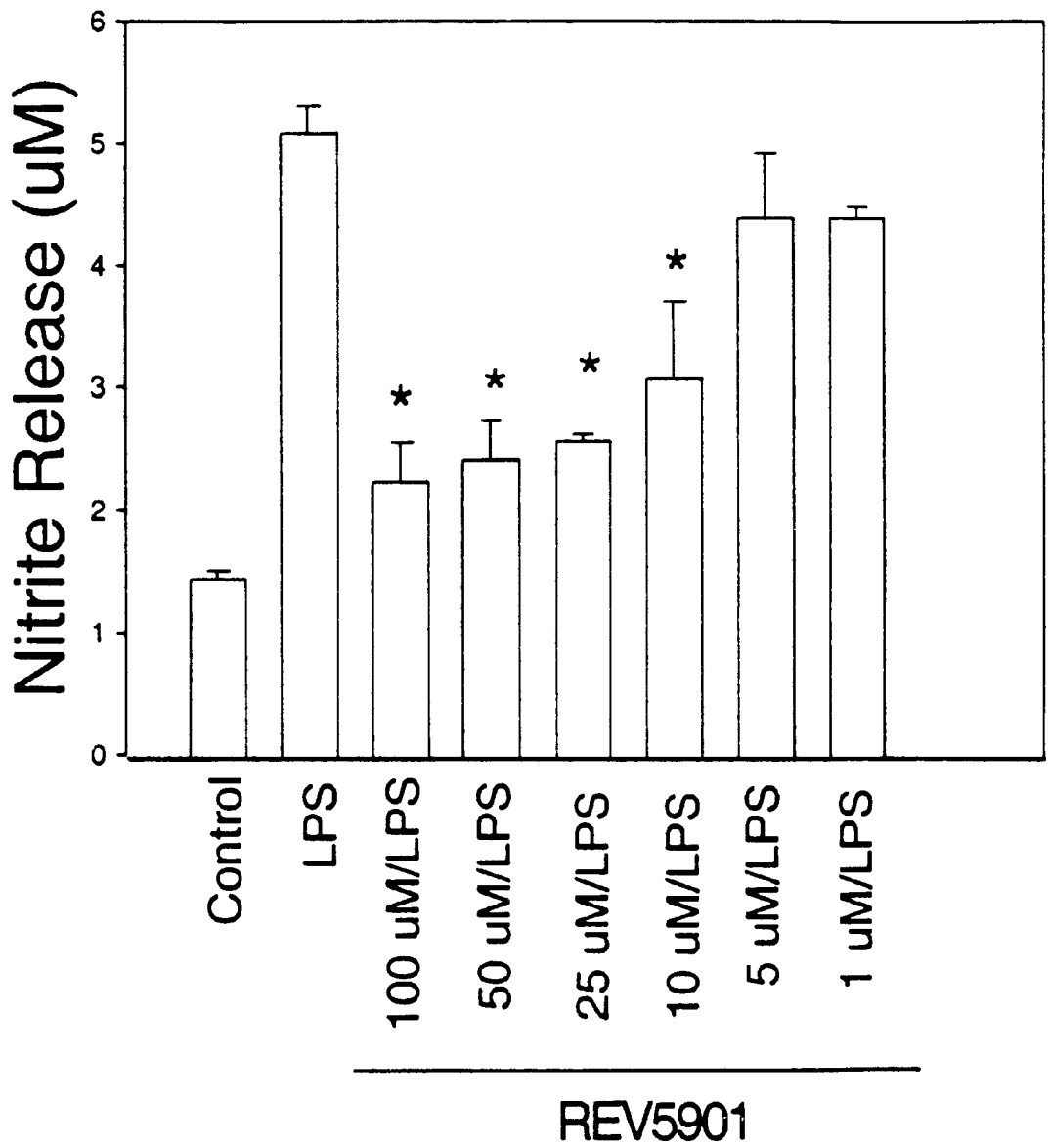
Figure 4C:
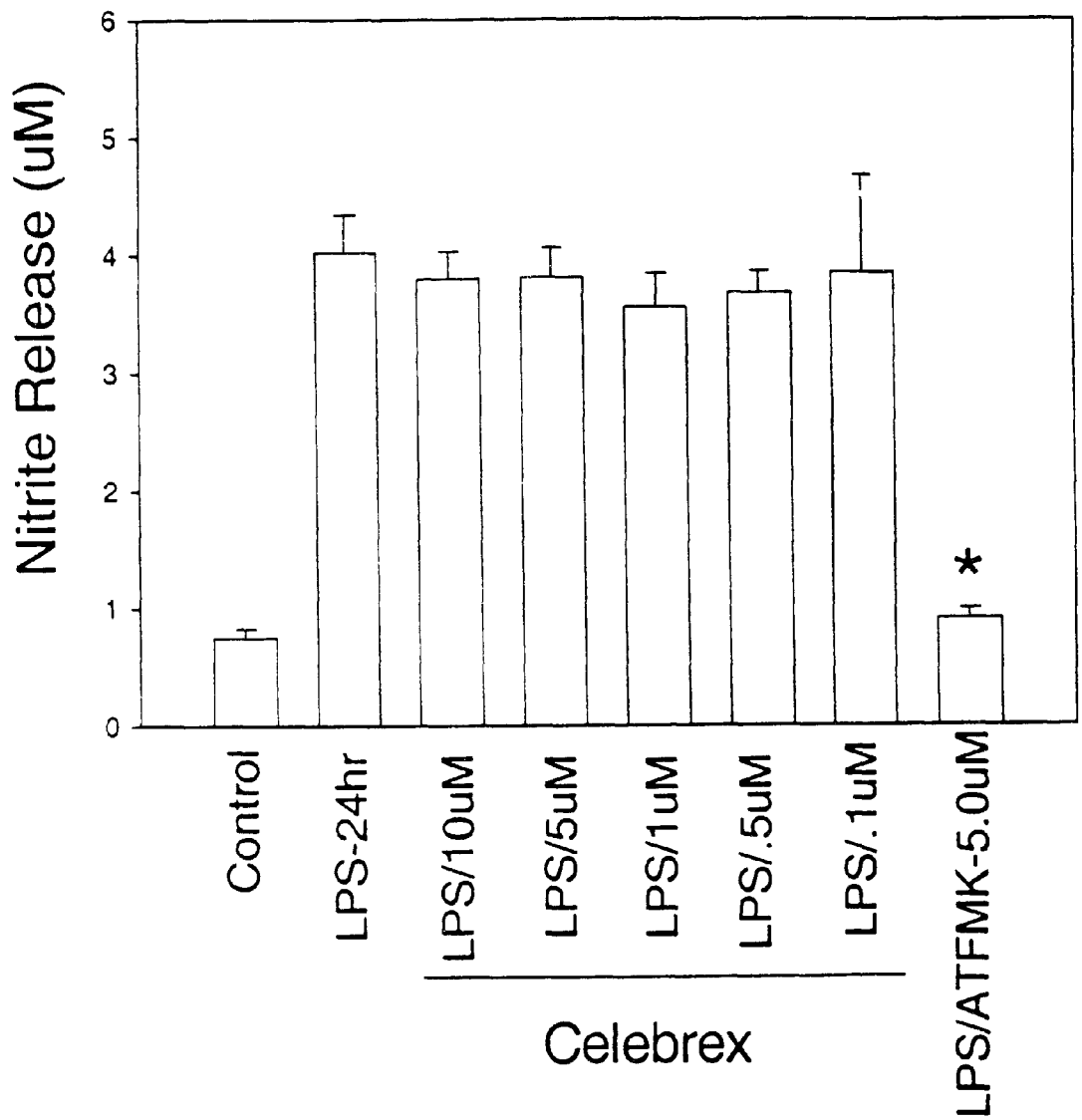

FIGS. 4A–C Legend cPLA2 inhibitor, ATFMK (4A) and FLAP inhibitor, para-REV5901 (4B) significantly inhibited nitrite release in rat primary microglia cells following LPS activation. However, COX-2 inhibitor, Celebrex (4C) had no effect on nitrite release.

Figure 5A:
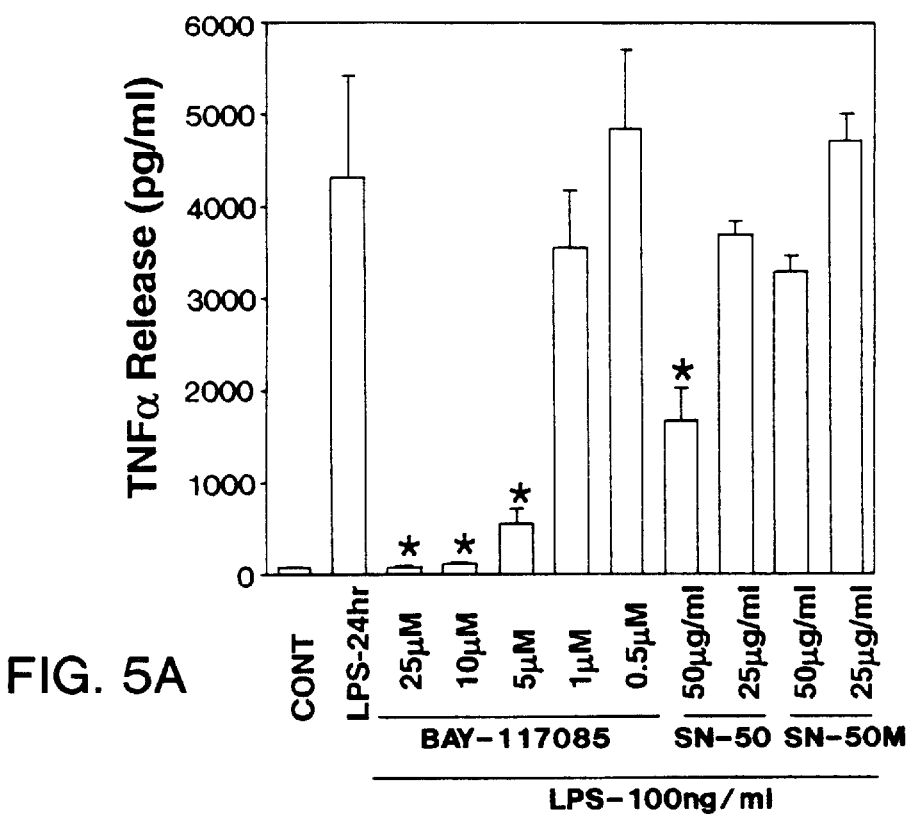
Figure 5B:
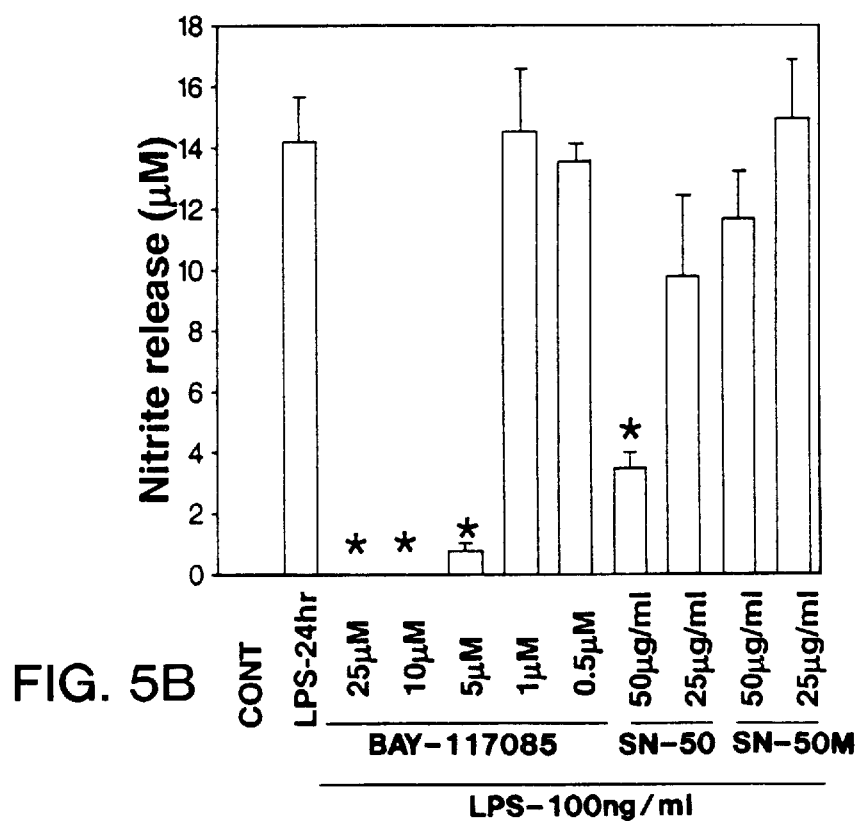

FIGS. 5A–B Legend

Effects of NF-κB inhibitors, BAY 11–7085 and SN-50 on TNFα and NO release in LPS treated microglia. Microglia were treated with various concentrations of either BAY- or SN-50 for one hour prior to the addition of LPS. Twenty-four hours post LPS challenge the media was assayed for TNFα release by ELISA (5A) and nitrite release by modified Greiss reagent (5B).

Figure 6A:
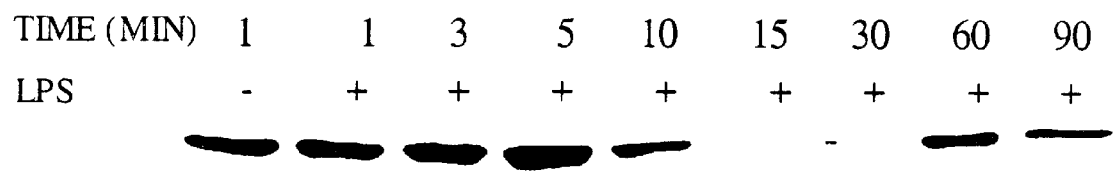
Figure 6B:
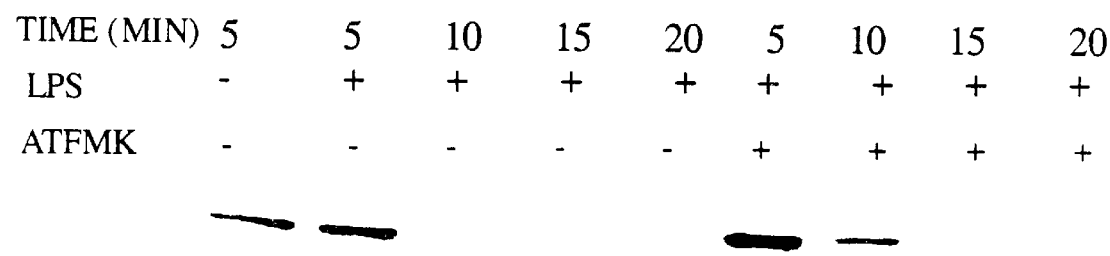
Figure 6C:
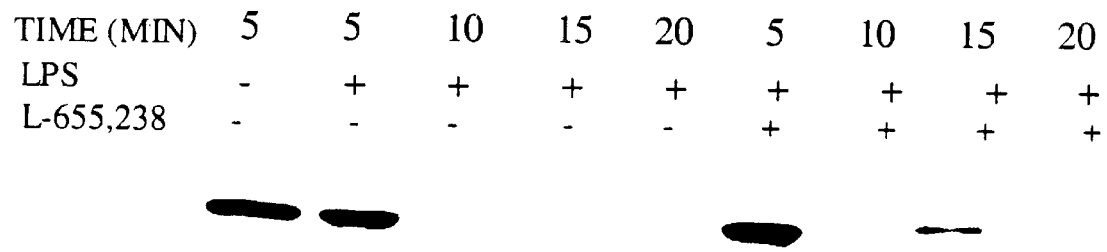
Figure 7A:
Figure 7B:
Figure 7C:
Figure 7D:
Figure 7E:

FIGS. 6A–C Legend

Effects of cPLA$_2$ and 5-LOX inhibitors on LPS mediated IκBα degradation. Microglia were treated with 100 ng/ml of LPS for various periods of time following which whole cell lysates were prepared and run on SDS-PAGE, transferred and probed with a IκBα antibody as mentioned in immunoblotting. (6A) 100 ng/ml LPS alone, (6B) LPS+10μM ATFMK, (6C) LPS+50μM L-655,238.

FIGS. 7 A–E Legend

Effects of cPLA$_2$ and 5-LOX inhibitors on LPS mediated NF-κB translocation. Microglia were treated with 100 ng/ml of LPS for various periods of time following which p65 distribution was assessed by indirect immunofluorescence (7A) control, (7B) LPS-5 min., (7C) LPS+10μM ATFMK—5 min., (7D) LPS+50μM L-655,238—5 min. (7E) LPS+NDGA-20μM—5 min.

Figure 8:
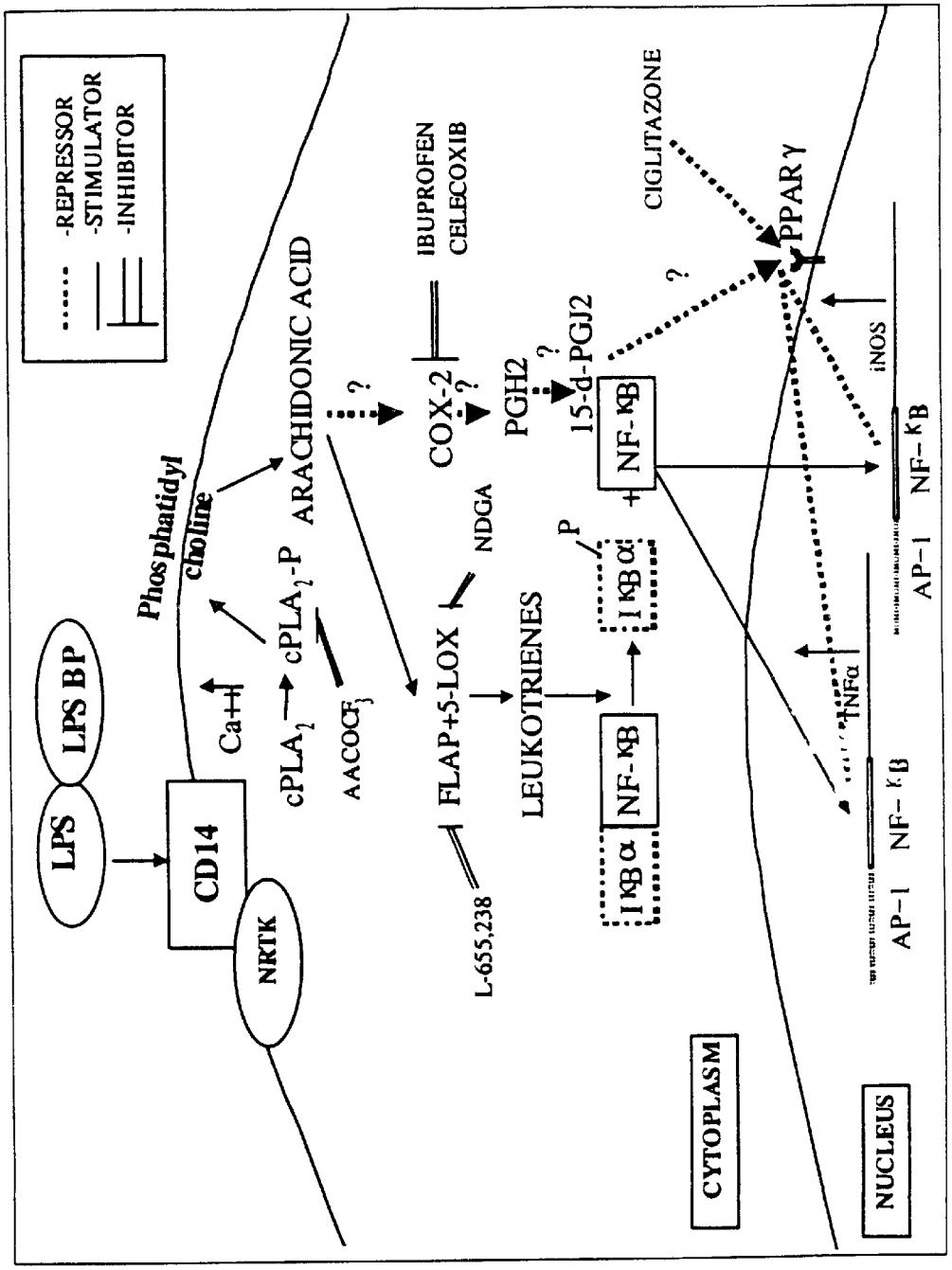

FIG. 8 illustrates in schematic form the role of 5-LOX in LPS (lipopolysaccharide) induced microglia activation.

What is claimed is:

1. A method of modulating microglia activation comprising the administration to a human in need thereof

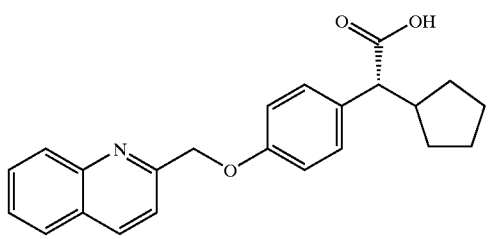

or a pharmaceutically acceptable salt or solvate thereof.

2. A method of inhibiting the release of pro-inflammatory substances from activated microglial cells comprising the administration to a human in need thereof

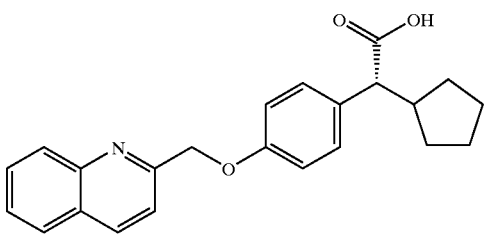

or a pharmaceutically acceptable salt or solvate thereof.

3. A method of treating Alzheimer's disease comprising the administration to a human in need thereof

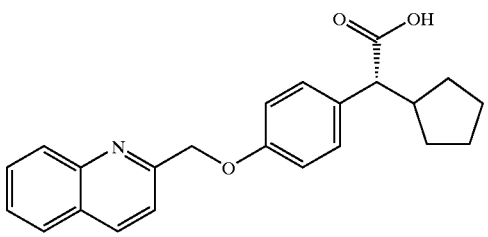

or a pharmaceutically acceptable salt or solvate thereof.

4. A method of attenuating degradation of IκBα comprising the administration to a human in need thereof

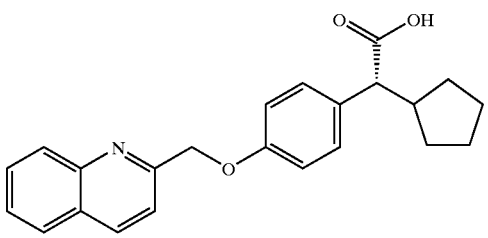

or a pharmaceutically acceptable salt or solvate thereof.

5. A method of inhibiting nuclear translocation of the NF-κB active complex comprising the administration to a human in need thereof

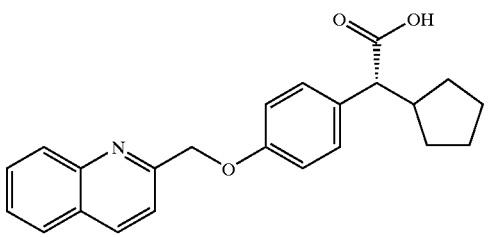

or a pharmaceutically acceptable salt or solvate thereof.

* * * * *